United States Patent [19]

Rosen et al.

[11] Patent Number: 5,939,388
[45] Date of Patent: Aug. 17, 1999

[54] METHODS OF ADMINISTERING BMP-5 COMPOSITIONS

[76] Inventors: Vicki A. Rosen, 2 Cedar Rd., Chestnut Hill, Mass. 02167; John M. Wozney, 59 Old Bolton Rd., Hudson, Mass. 01749; Elizabeth A. Wang, 125 Judy Farm Rd., Carlisle, Mass. 01741

[21] Appl. No.: 08/788,729

[22] Filed: Jan. 23, 1997

Related U.S. Application Data

[60] Continuation-in-part of application No. 08/469,935, Jun. 6, 1995, Pat. No. 5,635,373, which is a division of application No. 08/116,425, Sep. 7, 1993, Pat. No. 5,543,394, which is a continuation of application No. 07/995,565, Dec. 22, 1992, abandoned, which is a continuation of application No. 07/588,227, Sep. 26, 1990, abandoned, which is a continuation-in-part of application No. 07/437,409, Nov. 15, 1989, abandoned, which is a continuation-in-part of application No. 07/370,547, Jun. 23, 1989, Pat. No. 5,106,748, which is a continuation of application No. 07/347,559, May 4, 1989, abandoned, which is a continuation-in-part of application No. 07/329,610, Mar. 28, 1989, abandoned, which is a continuation-in-part of application No. 07/179,100, Apr. 8, 1988, Pat. No. 5,013,649, and a continuation-in-part of application No. 07/179,101, Apr. 8, 1988, abandoned, and a continuation-in-part of application No. 07/179,197, Apr. 8, 1988, abandoned, said application No. 07/179,100, Apr. 8, 1988, Pat. No. 5,013,649, said application No. 07/179,101, Apr. 8, 1988, abandoned, said application No. 07/179,197, Apr. 8, 1988, abandoned, and a continuation-in-part of application No. 07/028,285, Mar. 20, 1987, abandoned, and a continuation-in-part of application No. 07/031,346, Mar. 26, 1987, Pat. No. 4,877,864, said application No. 07/028, 285, Mar. 20, 1987, abandoned, said application No. 07/031, 346, Mar. 26, 1987, Pat. No. 4,877,864, and a continuation-in-part of application No. 06/943,332, Dec. 17, 1986, abandoned, and a continuation-in-part of application No. 06/880,776, Jul. 1, 1986, abandoned.

[51] Int. Cl.[6] .................. A61K 38/16; A61K 38/18
[52] U.S. Cl. .................. 514/12; 514/2; 424/85.1
[58] Field of Search ................ 514/2, 12; 424/85.1

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69 |
| 4,968,590 | 11/1990 | Kuberasampath et al. | 530/326 |
| 5,011,691 | 4/1991 | Oppermann | 424/423 |
| 5,106,626 | 4/1992 | Parsons et al. | 424/423 |
| 5,108,753 | 4/1992 | Kuberasampath | 424/422 |

FOREIGN PATENT DOCUMENTS

| | | | |
|---|---|---|---|
| 2 017466 | 5/1990 | Canada | C12N 15/16 |
| 33 6760 A2 | 6/1989 | European Pat. Off. | C07K 7/00 |
| 4 165 78A2 | 5/1990 | European Pat. Off. | C12N 15/00 |
| 4 094 72 A1 | 11/1990 | European Pat. Off. | C12N 15/12 |
| WO 89/09787 | 10/1989 | WIPO | C07K 13/00 |
| WO 89/09788 | 10/1989 | WIPO | C07K 13/00 |
| WO 90/03733 | 4/1990 | WIPO | A01N 63/02 |
| WO 91/02744 | 3/1991 | WIPO | C07K 15/06 |
| WO 91/05802 | 5/1991 | WIPO | C07K 15/00 |
| WO 91/18047 | 11/1991 | WIPO | C08J 7/18 |

OTHER PUBLICATIONS

Kingsley et al. Cell 71:399–410, Oct. 1992.
DiLeone et al. Genetics 148:401–8, Jan. 1998.
Kingsley Genes & Dev'p. 8:133–46, 1994.
Urist et al., *Science* 220:680–686 (1983).
Luyten et al., *The Journal of Biological Chemistry* 264(23):13377–13380 (Aug. 15, 1989).
Sampath, et al., *Proc. Natl Acad. Sci* 84:7109–7113 (1987).
Ozkaynak et al., *The EMBO Journal* v.9 No.7:2085–2093 (1990).
Lyons et al., *Proc. Natl. Acad. Sci (USA)* 86:4554–4558 (Jun. 1989).
Hammonds et al., *Molecular Endocrinology* 5:149–155 (1991).

*Primary Examiner*—Elizabeth Kemmerer
*Attorney, Agent, or Firm*—Ellen J. Kapinos

[57] ABSTRACT

Purified BMP-5 proteins and processes for producing them are disclosed. The proteins may be used in the treatment of bone and/or cartilage defects and in wound healing and related tissue repair.

2 Claims, No Drawings

METHODS OF ADMINISTERING BMP-5 COMPOSITIONS

CROSS-REFERENCE TO RELATED APPLICATIONS

This application is a continuation-in-part of U.S. Ser. No. 08/469,935, filed Jun. 6, 1995, now U.S. Pat. No. 5,635,373, which is a divisional of U.S. Ser. No. 08/116,425, filed Sep. 7, 1993, now U.S. Pat. No. 5,543,394, which is a continuation of U.S. Ser. No. 07/995,565, filed Dec. 22, 1992, now abandoned, which is a continuation of U.S. Ser. No.07/588,227, filed Sep. 26, 1990, now abandoned, which is a continuation-in-part of U.S. Ser. No. 07/437,409, filed Nov. 15, 1989, now abandoned; which is a continuation-in-part of U.S. Ser. No. 07/370,547, filed Jun. 23, 1989, now U.S. Pat. No. 5,106,748; which is a continuation-in-part of U.S. Ser. No. 07/347,559, filed May 4, 1989, now abandoned; which is a continuation-in-part of U.S. Ser. No. 07/329,610, filed Mar. 28, 1989, now abandoned, which is a continuation-in-part of U.S. Ser. No. 07/179,100, now U.S. Pat. No. 5,013,649, U.S. Ser. No. 07/179,101, now abandoned, and U.S. Ser. No. 07/179,197, now abandoned; each filed Apr. 8, 1988, which are continuations-in-part of U.S. Ser. No. 07/028,285, filed Mar. 20, 1987, now abandoned, and U.S. Ser. No. 07/031,346, filed Mar. 26, 1987, now U.S. Pat. No. 4,877,864, which are continuations-in-part of U.S. Ser. No. 06/943,332, filed Dec. 17, 1986, now abandoned, and Ser. No. 06/880,776, filed Jul. 1, 1986, now abandoned.

DESCRIPTION OF THE INVENTION

The present invention relates to a family of purified proteins, termed BMP-5 proteins (wherein BMP is bone morphogenic protein), which exhibit the ability to induce cartilage and/or bone formation and processes for obtaining them. These proteins may be used to induce bone and/or cartilage or other connective tissue formation and in wound healing and tissue repair.

The invention provides human BMP-5 proteins, substantially free from other proteins with which they are co-produced, comprising the amino acid sequence set forth in Table III from amino acid #317 (Ala, Ala, Asn) to amino acid #454 (ending with Gly, Lys, His). The amino acid sequence of Table III #317 to #454 is encoded by the nucleotide sequence of Table III from #1647 to #2060. In another embodiment, the protein comprises amino acid #323 (Asn, Gln, Asn) to amino acid #454 (ending with Gly, Cys, His). This amino acid sequence #323 to #454 is encoded by the DNA sequence of Table III from nucleotide #1665 to nucleotide #2060. The mature BMP-5 dimer may be further characterized by an apparent molecular weight of approximately 28,000–38,000 daltons as determined by sodium dodecyl sulfate polyacrylamide gel electrophoresis (SDS-PAGE). Under reducing conditions in SDS-PAGE the mature subunit electrophoreses with a molecular weight of approximately 18,000–22,000 daltons. These proteins are capable of stimulating, promoting, or otherwise inducing cartilage and/or bone formation.

The invention further provides bovine BMP-5 proteins comprising the amino acid sequence set forth in Table I from #9 to amino acid #140. The amino acid sequence from #9 to #140 is encoded by the DNA sequence from nucleotide # 32 to #427 of Table I. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of inducing cartilage and/or bone formation.

Human BMP-5 proteins of the invention may be produced by culturing a cell transformed with a DNA sequence containing the nucleotide sequence the same or substantially the same as the nucleotide sequence shown in Table III comprising nucleotide #699 to nucleotide #2060. BMP-5 proteins comprising the amino acid sequence the same or substantailly the same as shown in Table III from amino acid #317 to #954 or in other embodiments from amino acid #323 to #454, are recovered isolated and purified from the culture media.

Bovine proteins of the invention may be produced by culturing a cell transformed with a DNA sequence containing the nucleotide sequence the same or substantially the same as that shown in Table I comprising nucleotide #8 through nucleotide #427 and recovering and purifying from the culture medium a protein containing the amino acid sequence or a portion thereof as shown in Table I comprising amino acid #9 to amino acid #140.

The invention further provides a method wherein the proteins described above are utilized for obtaining related human protein/s or other mammalian cartilage and/or bone growth protein/s. Such methods are known to those skilled in the art of genetic engineering. One method for obtaining such proteins involves utilizing the human BMP-5 coding sequence or portions thereof from nucleotide # 699–# 2060 as a probe for screening human genomic and/or cDNA libraries to isolate the human genomic and/or cDNA sequence. Additional methods known in the art may employ the bovine and human BMP-5 proteins of the invention to obtain other mammalian BMP-5 cartilage and/or bone formation proteins.

Having identified the nucleotide sequences the proteins are produced by culturing a cell transformed with the DNA identified in the method described above which DNA hybridizes under stringent conditions to the bovine BMP-5 nucleotide sequence substantially as shown in Table I or the human BMP-5 nucleotide sequence substantially as shown in Table III and which encodes a protein exhibiting cartilage and/or bone formation activity. The expressed proteins are recovered and purified from the culture media. The purified BMP-5 proteins are substantially free from other proteinaceous materials with which they are co-produced, as well as from other contaminants.

The BMP-5 proteins of the invention are characterized by the ability to promote, stimulate or otherwise induce the formation of cartilage and/or bone. It is further contemplated that the ability of these proteins to induce the formation of cartilage and/or bone may be exhibited by the ability to demonstrate cartilage and/or bone formation and/or other connective tissue formation activity in the rat bone formation assay described below. It is further contemplated that the proteins of the invention may demonstrate activity in this rat bone formation assay at a concentration of 10 lg–500 lg/gram of bone. More particularly, it is contemplated these proteins may be characterized by the ability of 1 lg of the protein to score at least +2 in the rat bone formation assay described below using either the original or modified scoring method.

Another aspect of the invention provides pharmaceutical compositions containing a therapeutically effective amount of a BMP-5 protein of the invention in a pharmaceutically acceptable vehicle or carrier. The compositions of the invention may be used to induce bone and/or cartilage and/or other connective tissue formation. These compositions may also be used for wound healing and tissue repair. The compositions of the invention may also be useful for treating cell populations, such as embryonic cells or stem cell populations, to enhance or enrich the growth and/or differentiation of the cells. Further compositions of the invention may include in addition to a BMP-5 protein of the present invention at least one other therapeutically useful agent such as the proteins designated BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035, or BMP-15, disclosed in co-pending patent application, Ser. No. 08/446,924, filed on May 18, 1995. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of the above applications are hereby incorporated by reference. These proteins may act in concert with or perhaps synergistically with one another. Other therapeutically useful agents may include growth factors such as epidermal growth factor (EGF), fibroblast growth factor (FGF), transforming growth factors (TGF-a and TGF-b), and platelet derived growth factor (PDGF)and activins, inhibins, and insulin-like growth factor (IGF).

The compositions of the invention may also include an appropriate matrix, for instance, for delivery and/or support of the composition and/or providing a surface for bone and/or cartilage formation. The matrix may provide slow release of the BMP-5 proteins and/or the appropriate environment for presentation of the BMP-5 proteins of the invention.

The compositions may be employed in methods for treating a number of bone and/or cartilage defects and/or other connective tissue defects, and periodontal disease. They may also be employed in methods for treating various types of wounds and in tissue repair. The tissue and wounds which may be treated include epidermis, nerve, muscle, including cardiac muscle, and other tissues and wounds, and other organs such as liver, lung, cardiac, pancreas and kidney tissue. These methods, according to the invention, entail administering to a patient needing such bone and/or cartilage formation, wound healing or tissue repair, a therapeutically effective amount of a protein of the invention. The BMP-5 containing compositions may also be used to treat or prevent such conditions as osteoarthritis, osteoporosis, and other abnormalities of bone, cartilage, muscle, tendon, ligament or other connective tissue, organs such as liver, lung, cardiac, pancreas and kidney tissue, and other tissues. These methods may also entail the administration of a protein of the invention in conjunction with at least one of the "BMP" proteins disclosed in the co-owned applications described above. In addition, these methods may also include the administration of a protein of the invention with other growth factors including EGF, FGF, TGF-a, TGF-b, and PDGF.

Still a further aspect of the invention are DNA sequences coding for expression of a protein of the invention. Such sequences include the sequence of nucleotides in a 5' to 3' direction illustrated in Table I or Table III or DNA sequences which hybridize under stringent conditions with the DNA sequence of Table I or Table III and encode a protein demonstrating ability to induce cartilage and/or bone formation and/or other connective tissue, as in the rat bone formation assay described below. For production in mammalian cells, the DNA sequence further comprises a DNA sequence encoding a suitable propeptide 5' to and linked in frame to the nucleotide sequence encoding the mature BMP-5-related polypeptide. The propeptide may be the native BMP-5-related propeptide, or may be a propeptide from another protein of the TGF-β superfamily. It is contemplated that these proteins may demonstrate activity in this assay at a concentration of 10 lg–500 lg/gram of bone. More particularly, it is contemplated that these proteins demonstrate the ability of 1 lg of the protein to score at least +2 in the rat bone formation assay using either the original or modified scoring method. Finally, allelic or other variations of the sequences of Table I and III whether such nucleotide changes result in changes in the peptide sequence or not, are also included in the present invention.

A further aspect of the invention provides a vector containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is recovered and purified therefrom. This claimed process may employ a number of known cells, both prokaryotic and eukaryotic, as host cells for expression of the polypeptide. The recovered BMP protiens are purified by isolating them from other proteinaceous materials with which they are co-produced as well as from other contaminants.

Other aspects and advantages of the present invention will be apparent upon consideration of the following detailed description and preferred embodiments thereof.

DETAILED DESCRIPTION OF THE INVENTION

Purified human BMP-5 proteins are produced by culturung a host cell transformed with the DNA sequence of Table III. The expressed BMP-5 proteins are isolated and purified from the culture media. The purified human BMP-5 proteins are characterized by comprising an amino acid sequence as shown in Table III from amino acid #323 to #454. These purified BMP-5 human cartilage/bone proteins of the present invention may be produced by culturing a host cell transformed with a DNA sequence comprising the DNA sequence as shown in Table III from nucleotide # 699 to nucleotide # 2060 or substantially homologous sequences operatively linked to a heterologous regulatory control sequence and recovering and purifying from the culture medium a protein comprising the amino acid sequence as shown in Table III from amino acid # 323 to amino acid # 454 or a substantially homologous sequence.

In further embodiments the DNA sequence comprises the nucleotides encoding amino acids #323–#454 of Table III. BMP-5 proteins may therefore be produced by culturing a host cell transformed with a DNA sequence comprising the DNA sequence as shown in Table III from nucleotide # 1665 to nucleotide # 2060 or substantially homologous sequences operatively linked to a heterologous regulatory control sequence and recovering and purifying from the culture medium a protein comprising the amino acid sequence as shown in Table III from amino acid # 323 to amino acid # 454 or a substantially homologous sequence. The purified human BMP-5 proteins are substantially free from other proteinaceous materials with which they are co-produced, as well as from other contaminants.

Purified BMP-5 bovine cartilage/bone proteins of the present invention are produced by culturing a host cell transformed with a DNA sequence comprising the DNA sequence as shown in Table I from nucleotide # 8 to nucleotide # 578 or substantially homologous sequences and recovering and purifying from the culture medium a protein comprising the amino acid sequence as shown in Table I from amino acid # 9 to amino acid # 140 or a substantially homologous sequence. The purified BMP-5 bovine proteins of the invention are substantially free from other proteinaceous materials with which they are co-produced, as well as from other contaminants.

BMP-5 proteins are further characterized by the ability to demonstrate cartilage and/or bone formation activity. This activity may be demonstrated, for example, in the rat bone formation assay as described in Example III. It is further contemplated that these proteins demonstrate activity in the assay at a concentration of 10 lg–500 lg/gram of bone formed. The proteins may be further characterized by the ability of 1 lg to score at least +2 in this assay using either the original or modified scoring method described below.

The mature BMP-5 dimer may be further characterized by an apparent molecular weight of approximately 28,000–38,000 daltons as determined by sodium dodecyl sulfate polyacrylamide gel electrophoresis (SDS-PAGE). Under reducing conditions in SDS-PAGE the mature sub-unit electrophoreses with a molecular weight of approximately 18,000–22,000 daltons.

The proteins provided herein also include factors encoded by the sequences similar to those of Table I and Table III but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of Table I or Table III are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein may involve modifications of a glycosylation site. These modification may involve O-linked or N-linked glycosylation sites. For instance, the absence of glycosylation or only partial glycosylation at asparagine-linked glycosylation sites results from amino acid substitution or deletion at any asparagine-linked glycosylation recognition site present in the sequences of the proteins of the invention, for example, as shown in Table I or Table III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

The present invention also encompasses the novel DNA sequences, free of association with DNA sequences encoding other proteinaceous materials, and coding on expression for the proteins of the invention. These DNA sequences include those depicted in Tables I and III in a 5' to 3' direction. Further included are those sequences which hybridize under stringent hybridization conditions [see, T. Maniatis et al, *Molecular Cloning* (*A Laboratory Manual*), Cold Spring Harbor Laboratory (1982), pages 387 to 389] to the DNA sequence of Table I or Table III and encode a protein which demonstrates cartilage and/or bone and/or other connective tissue formation activity for example in the rat bone formation assay, or induces the formation of other organs such as liver, lung, cardiac, pancreas and kidney tissue. An example of one such stringent hybridization condition is hybridization at 4×SSC at 65° C., followed by a washing in 0.1×SCC at 65° C. for an hour. Alternatively, an exemplary stringent hybridization condition is in 50% formamide, 4×SCC at 42° C.

Similarly, DNA sequences which encode proteins similar to the protein encoded by the sequence of Table I or Table III, but which differ in codon sequence due to the degeneracies of the genetic code or allelic variations (naturally-occurring base changes in the species population which may or may not result in an amino acid change) also encode the proteins of the invention described herein. Variations in the DNA sequences of Table I and Table III which are caused by point mutations or by induced modifications (including insertion, deletion, and substitution) to enhance the activity, half-life or production of the polypeptides encoded thereby are also encompassed in the invention.

The DNA sequences of the present invention are useful, for example, as probes for the detection of mRNA encoding BMP-5 in a given cell population. Thus, the present invention includes methods of detecting or diagnosing genetic disorders involving the BMP-5 gene, or disorders involving cellular, organ or tissue disorders in which BMP-5 is irregularly transcribed or expressed. The DNA sequences may also be useful for preparing vectors for gene therapy applications as described below.

In a further aspect, the invention provides a method for obtaining related human proteins or other mammalian BMP-5 proteins. One method for obtaining such proteins entails, for instance, utilizing the human BMP-5 coding sequence disclosed herein to probe a human genomic library using standard techniques for the human gene or fragments thereof. Sequences thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity in the rat bone formation assay of Example III.

Another aspect of the present invention provides a novel method for producing the proteins of the invention. The method of the present invention involves culturing a suitable cell line, which has been transformed with a DNA sequence coding for expression of a protein of the invention, under the control of known regulatory sequences. Regulatory sequences include promoter fragments, terminator fragments and other suitable sequences which direct the expression of the protein in an appropriate host cell. Methods for culturing suitable cell lines are within the skill of the art. The transformed cells are cultured and the BMP-5 proteins expressed thereby are recovered and purified from the culture medium using purification techniques known to those skilled in the art. The purified BMP-5 proteins are substantially free from other proteinaceous materials with which they are co-produced, as well as other contaminants. Purified BMP-5 proteins are substantially free from materials with which the proteins of the invention exist in nature.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines are the monkey COS-1 cell line and the CV-1 cell line.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of the proteins of the invention. The vectors contain the novel DNA sequences described above which code for the novel cartilage/bone proteins of the invention. Additionally the vectors also contain appropriate expression control sequences permitting expression of the protein sequences. Alternatively, vectors incorporating truncated or modified sequences as described above are also embodiments of the present invention and useful in the production of the proteins of the invention. Additionally, the sequence of Table III or other sequences encoding BMP-5 proteins could be manipulated to express a mature BMP-5 protein by deleting BMP-5 propeptide sequences and replacing them with sequences encoding the complete propeptides of other BMP proteins or members of the TGF-β superfamily. Thus, the present invention includes chimeric DNA molecules encoding a propeptide from a member of the TGF-β superfamily linked in correct reading frame to a DNA sequence encoding a BMP-5 polypeptide.

The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection. Host cells transformed with such vectors and progeny thereof for use in producing cartilage/bone proteins are also provided by the invention.

One skilled in the art can construct mammalian expression vectors by employing the DNA sequences of the invention and known vectors, such as pCD [Okayama et al., *Mol. Cell Biol.*, 2:161–170 (1982)] and pJL3, pJL4 [Gough et al., *EMBO J.*, 4:645–653 (1985)].

Similarly, one skilled in the art could manipulate the sequences of the invention by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For instance, a plasmid containing a DNA sequence for a protein of the invention in operative association with other plasmid sequences enabling expression thereof and the DHFR expression plasmid pAdA26SV(A)3 [Kaufman and Sharp, *Mol. Cell. Biol.*, 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Protein expression should increase with increasing levels of MTX resistance. Transformants are cloned, and the proteins of the invention are recovered, isolated, and purified from the culture medium. Characterization of expressed proteins may be carried out using standard techniques. For instance, characterization may include pulse labeling with [$35^S$]

methionine or cysteine, or polyacrylamide gel electrphoresis. Biologically active protein expression is monitored by the Rosen-modified Sampath-Reddi rat bone formation assay described above in Example III. Similar procedures can be followed to produce other related proteins.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells, and may also support the regeneration of the peridontal ligament and attachment apparatus, which connects bone and teeth. BMP-5 polypeptides of the invention may also be useful in the treatment of osteoporosis. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, lung, cardiac, pancreas and kidney tissue. The proteins of the present invention may further be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

The proteins of the invention may also have other useful properties characteristic of the TGF-β superfamily of proteins. Such properties include angiogenic, chemotactic and/or chemoattractant properties, and effects on cells including induction of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formation.

When dimerized as a homodimer or as a heterodimer with other BMPs, with other members of the TGF-β superfamily of proteins, or with inhibin-α proteins or inhibin-β proteins, the BMP-5 heterodimer is expected to demonstrate effects on the production of follicle stimulating hormone (FSH), as described further herein. It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, BMP-5 may be useful as a contraceptive based on the ability of inhibins to decrease fertility in female mammals and decrease spermatogenesis in male mammals. Administration of sufficient amounts of other inhibins can induce infertility in mammals. BMP-5 may also be useful as a fertility inducing therapeutic, based upon the ability of activin molecules in stimulating FSH release from cells of the anterior pituitary. See, for example, U.S. Pat. No. 4,798,885. BMP-5 may also be useful for advancement of the onset of fertility in sexually immature mammals, so as to increase the lifetime reproductive performance of domestic animals such as cows, sheep and pigs. It is further contemplated that BMP-5 may be useful in modulating hematopoiesis by inducing the differentiation of erythroid cells [see, e.g., Broxmeyer et al, Proc. Natl. Acad. Sci. USA, 85:9052–9056 (1988) or Eto et al, Biochem. Biophys. Res. Comm., 142:1095–1103 (1987)], for suppressing the development of gonadal tumors [see, e.g., Matzuk et al., Nature, 360:313–319 (1992)] or for augmenting the activity of bone morphogenetic proteins [see, e.g., Ogawa et al., J. Biol. Chem., 267:14233–14237 (1992)].

BMP-5 proteins may be further characterized by their ability to modulate the release of follicle stimulating hormone (FSH) in established in vitro bioassays using rat anterior pituitary cells as described [see, e.g., Vale et al, Endocrinology, 91:562–572 (1972); Ling et al., Nature, 321:779–782 (1986) or Vale et al., Nature, 321:776–779 (1986)]. It is contemplated that the BMP-5 protein of the invention, when composed as a heterodimer with inhibin α or inhibin β chains, will exhibit regulatory effects, either stimulatory or inhibitory, on the release of follicle stimulating hormone (FSH), from anterior pituitary cells as described [Ling et al., Nature, 321:779–782 (1986) or Vale et al., Nature, 321:776–779 (1986); Vale et al, Endocrinology, 91:562–572 (1972). Therefore, depending on the particular composition, it is expected that the BMP-5 protein of the invention may have contrasting and opposite effects on the release of follicle stimulating hormone (FSH) from the anterior pituitary.

Activin A (the homodimeric composition of inhibin $\beta_A$) has been shown to have erythropoietic-stimulating activity [see e.g. Eto et al., Biochem. Biophys. Res. Commun., 142:1095–1103 (1987) and Murata et al., Proc. Natl. Acad. Sci. U.S.A., 85:2434–2438 (1988) and Yu et al., Nature, 330:765–767 (1987)]. It is contemplated that the BMP-5 protein of the invention may have a similar erythropoietic-stimulating activity. This activity of the BMP-5 protein may be further characterized by the ability of the BMP-5 protein to demonstrate erythropoietin activity in the biological assay performed using the human K-562 cell line as described by [Lozzio et al., Blood, 45:321–334 (1975) and U.S. Pat. No. 5,071,834].

A further aspect of the invention includes a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the BMP-5 proteins of the invention in admixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; BMP- 11, disclosed in PCT application WO94/26892, BMP-12 or BMP-13, disclosed in PCT application WO 95/16035, or BMP-15, disclosed in co-pending patent application, Ser. No. 08/446, 924, filed on May 18, 1995. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein.

It is expected that human BMP-5 protein may exist in nature as homodimers or heterodimers. To promote the formation of dimers of BMP-5 and useful proteins with increased stability, one can genetically engineer the DNA sequence of Table III to provide one or more additional cysteine residues to increase potential dimer formation. The resulting DNA sequence would be capable of producing a "cysteine added variant" of BMP-5. In a preferred embodiment, one would engineer the DNA sequence of Table III so that one or more codons may be altered to a nucleotide triplet encoding a cysteine residue, such as TGT or TGC. Alternatively, one can produce "cysteine added variants" of BMP-5 protein by altering the sequence of the protein at the amino acid level by altering one or more amino acid residues of Table III to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins, BMP-1, BMP-2 (BMP-2A, BMP-2 Class I), BMP-3, BMP-4(BMP-2B, BMP-2 Class II), BMP-6, and BMP-7 disclosed in co-owned and co-pending U.S. applications described above. Such methods and compositions of the invention may comprise proteins of the invention or portions thereof in combination with the above-mentioned "BMP" proteins or portions thereof. Such combination may comprise individual separate molecules from each of the proteins or heteromolecules such as heterodimers formed by portions of the respective proteins. For example, a method and composition of the invention may comprise a protein of the invention or a portion thereof linked with a portion of a "BMP" protein to form a heteromolecule. Thus, the present invention includes a purified BMP-5-related polypeptide which is a heterodimer wherein one subunit comprises the amino acid sequence from amino acid #317 to amino acid #454 of Table III, and one subunit comprises an amino acid sequence for a bone morphogenetic protein selected from the group consisting of BMP-1, BMP-2, BMP-3, BMP-4, BMP-6, BMP-7, BMP-8, BMP-9, BMP-10, BMP-11, BMP-12 or BMP-13, disclosed in PCT application WO 95/16035, or BMP-15, disclosed in co-pending patent application, Ser. No. 08/446,924, filed on May 18, 1995.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-a and TGF-b), k-fibroblast growth factor (kFGF), parathyroid hormone (PTH), leukemia inhibitory factor (LIF/HILDA DIA) and insulin-like growth factors (IGF-I and IGF-II). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone growth factor proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition would include a matrix capable of delivering the cartilage/bone proteins of the invention to the site of bone and/or cartilage damage, providing a structure for the developing bone and cartilage and optimally capable of being resorbed into the body. The matrix may provide slow release of the BMP proteins or other factors comprising the composition. Such matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-a, TGF-b, and IGF-I to the final composition, may also effect the dosage. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also affect the dosage.

Progress can be monitored by periodic assessment of cartilage and/or bone growth and/or repair. The progress can be monitored, for example, using x-rays, histomorphometric determinations and tetracycline labeling.

The purified proteins of the present inventions may be used to generate antibodies, either monoclonal or polyclonal, to human BMP-5 and/or other BMP-5-related proteins, using methods that are known in the art of antibody production. Thus, the present invention also includes antibodies to human BMP-5 and/or other related proteins. The antibodies may be useful for purification of BMP-5 and/or other BMP-5 related proteins, or for inhibiting or preventing the effects of BMP-5 related proteins.

The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilage/Bone Inductive Protein

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath-Reddi assay (described in Example III below) desorbed from the column by 50 mM NaAc, 0.25 mM NaCl, 6M urea (pH 4.6). The protein from this step elution is concentrated 20- to 40-fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin-Sepharose column equilibrated in 50 mM $KPO_4$, 150 mM NaCl, 6M urea (pH7.4). After extensive washing of the column with starting buffer, a protein with bone and/or cartilage inductive activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and/or bone formation activity. The active material from the C4 reverse phase column is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5 M NaCl, 6M urea, 25 mM diethanolamine, pH 8.6. Fractions are brought to pH3.0 with 10% trifluoroacetic acid (TFA).

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor

A. Molecular Weight

Approximately 5 lg protein from Example I in 6M urea, 25 mM diethanolamine, pH 8.6, approximately 0.3 M NaCl is made 0.1% with respect to SDS and dialyzed against 50 mM tris/HCl 0.1% SDS pH 7.5 for 16 hrs. The dialyzed material is then electrophorectically concentrated against a dialysis membrane [Hunkapillar et al Meth. Enzymol. 91: 227–236 (1983)] with a small amount of I 125 labelled counterpart. This material (volume approximately 100 ll) is loaded onto a 12% polyacrylamide gel and subjected to SDS-PAGE [Laemmli, U.K. Nature, 227:680–685 (1970)] without reducing the sample with dithiothreitol. The molecular weight is determined relative to prestained molecular weight standards (Bethesda Research Labs). Following autoradiography of the unfixed gel the approximate 28,000–30,000 dalton band is excised and the protein electrophoretically eluted from the gel (Hunkapillar et al supra). Based on similar purified bone fractions as described in the co-pending "BMP" applications described above wherein bone and/or cartilage activity is found in the 28,000–30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000–20,000 dalton region having a doublet appearance located by autoradiography of the unfixed gel. A faint band remains at the 28,000–30,000 region. Thus the 28,000–30,000 dalton protein yields a broad region of 14,000–20,000 which may otherwise also be interpreted and described as comprising two broad bands of approximately 14,000–16,000 and 16,000–20,000 daltons.

EXAMPLE III

Rosen Modified Sampath-Reddi Assay

A modified version of the rat bone formation assay described in Sampath and Reddi, Proc. Natl. Acad. Sci. U.S.A., 80:6591–6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 5–21 days. Half of each implant is used for alkaline phosphatase analysis [See, A. H. Reddi et al., Proc. Natl Acad Sci., 69:1601 (1972)].

The other half of each implant is fixed and processed for histological analysis. Glycolmethacrylate sections (1 lm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. The first describes the original scoring method while the second describes the later adopted scoring method. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The scoring method later adopted (which hereinafter may be referred to as the "modified" scoring method) is as follows: Three non-adjacent sections are evaluated from each implant and averaged. "±" indicates tentative indentification of cartilage or bone; "+1" indicates >10% of each section being new cartilage or bone; "+2", >25%; "+3", >50%; "+4", ~75%; "+5", >80%. A "–" indicates that the implant is not recovered. The scores of the individual implants are tabulated to indicate assay variability. It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI.

To estimate the purity of the protein in a particular fraction an extinction coefficient of 1 OD/mg-cm is used as an estimate for protein and the protein is run on SDS-PAGE followed by silver staining or radioiodination and autoradiography.

EXAMPLE IV

Bovine BMP-5 Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 lg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.

PROBE #1: GTRCTYGANATRCANTC
PROBE #2: GTRCTYGANATRCANAG
PROBE #3: GTRCTYAAYATRCANTC
PROBE #4: GTRCTYAAYATRCANAG

The standard nucleotide symbols in the above identified probes are as follows: A,adenine; C,cytosine; G,guanine; T,thymine; N, adenine or cytosine or guanine or thymine; R,adenine or guanine; and Y,cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in Skeletogenesis*, Elsevier Science Publishers (1985). The total RNA was obtained from Dr. Marion Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plague purified, a phage plate stock made, and bacteriophage DNA isolated. This DNA is digested with EcoRI and subcloned into M13 and pSP65 (Promega Biotec, Madison, Wis.) [Melton, et al., *Nucl. Acids Res.* 12:7035–7056 (1984)]. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in Table I from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in Table I from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications mentioned above. This fragment set forth in Table I is a portion of the DNA sequence which encodes a bovine BMP-5 protein of the invention. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of the bovine BMP-5 cartilage/bone protein of the invention.

TABLE I

```
     TCTAGAGGTGAGAGCAGCCAACAAGAGAAAAAATCAAAACCGCAATAAATCCGGCTCTCAT   61
    LeuGluValArgAlaAlaAsnLysArgLysAsnGlnAsnArgAsnLysSerGlySerHis
     (1)                                                 (15)

62 CAGGACTCCTCTAGAATGTCCAGTGTTGGAGATTATAACACCAGTGAACAAAAACAAGCC  121
     GlnAspSerSerArgMetSerSerValGlyAspTyrAsnThrSerGluGlnLysGlnAla
                    (23)

122 TGTAAAAAGCATGAACTCTATGTGAGTTTCCGGGATCTGGGATGGCAGGACTGGATTATA  181
     CysLysLysHisGluLeuTyrValSerPheArgAspLeuGlyTrpGlnAspTrpIleIle
              (42)

182 GCACCAGAAGGATATGCTGCATTTTATTGTGATGGAGAATGTTCTTTTCCACTCAATGCC  241
     AlaProGluGlyTyrAlaAlaPheTyrCysAspGlyGluCysSerPheProLeuAsnAla

242 CATATGAATGCCACCAATCATGCCATAGTTCAGACTCTGGTTCACCTGATGTTTCCTGAC  301
     HisMetAsnAlaThrAsnHisAlaIleValGlnThrLeuValHisLeuMetPheProAsp

302 CACGTACCAAAGCCTTGCTGCGCGACAAACAAACTAAATGCCATCTCTGTGTTGTACTTT  361
     HisValProLysProCysCysAlaThrAsnLysLeuAsnAlaIleSerValLeuTyrPhe

362 GATGACAGCTCCAATGTCATTTTGAAAAAGTACAGAAATATGGTCGTGCGTTCGTGTGGT  421
     AspAspSerSerAsnValIleLeuLysLysTyrArgAsnMetValValArgSerCysGly

422 TGCCACTAATAGTGCATAATAATGGTAATAAGAAAAAAGATCTGTATGGAGGTTTATGA  481
     CysHisEnd
       (140)

481 CTACAATAAAAAATATCTTTCGGATAAAAGGGGAATTTAATAAAATTAGTCTGGCTCATT  540

541 TCATCTCTGTAACCTATGTACAAGAGCATGTATATAGT                         578
```

The remaining positive clones isolated with probes #1, #2, #3, and #4 described above are screened with HEL5 and a further clone is identified that hybridizes under reduced hybridization conditions [5× SSC, 0.1% SDS, 5× Denhardt's, 100 lg/ml salmon sperm DNA standard hybridization buffer (SHB) at 65#C, wash in 2×SSC 0.1% SDS at 65#C]. This clone is plaque purified, a phage plate stock made and bacteriophage DNA isolated. The DNA sequence and derived amino acid sequence of a portion of this clone is shown in Table II. This sequence represents the DNA sequence encoding a BMP-6 cartilage/bone protein.

The first underlined portion of the sequence in Table II from amino acid #97–amino acid # 105 corresponds to the tryptic fragment found in the 28,000–30,000 dalton purified bovine bone preparation (and its reduced form at approximately 18,000–20,000 dalton reduced form) as described in the "BMP" co-pending applications mentioned above. The second underlined sequence in Table II from amino acid # 124–amino acid #130 corresponds to the tryptic fragment identified above from which the oligonucleotide probes are designed.

The DNA sequence of Table II indicates an open reading frame of 666 base pairs starting from the 5' end of the sequence of Table II, encoding a partial peptide of 222 amino acid residues. An in-frame stop codon (TGA) indicates that this clone encodes the carboxy-terminal part of a bovine BMP-6 protein of the invention. Based on knowledge of other BMP proteins and other proteins in the TGF-b family, it is predicted that the precursor polypeptide would be cleaved at the three basic residues (ArgArgArg) to yield a mature peptide beginning with residue 90 or 91 of the sequence of Table II.

TABLE II

```
         9              18             27             36             45             54
CTG CTG GGC ACG CGT GCT GTG TGG GCC TCA GAG GCG GGC TGG CTG GAG TTT GAC
Leu Leu Gly Thr Arg Ala Val Trp Ala Ser Glu Ala Gly Trp Leu Glu Phe Asp
(1)

63             72             81             90             99            108
ATC ACG GCC ACC AGC AAC CTG TGG GTC CTG ACT CCG CAG CAC AAC ATG GGG CTG
Ile Thr Ala Thr Ser Asn Leu Trp Val Leu Thr Pro Gln His Asn MET Gly Leu 117            126            135            144            153            162
CAG CTG AGC GTG GTC ACG CGT GAT GGG CTC AGC ATC AGC CCT GGG GCC GCG GGC
Gln Leu Ser Val Val Thr Arg Asp Gly Leu Ser Ile Ser Pro Gly Ala Ala Gly 171            180            189            198            207            216
CTG GTG GGC AGG GAC GGC CCC TAC GAC AAG CAG CCC TTC ATG GTG GCC TTC TTC
Leu Val Gly Arg Asp Gly Pro Tyr Asp Lys Gln Pro Phe MET Val Ala Phe Phe 225            234            243            252            261            270
AAG GCC AGT GAG GTC CAC GTG CGC AGT GCC CGG TCG GCC CCC GGG CGG CGC CGG
Lys Ala Ser Glu Val His Val Arg Ser Ala Arg Ser Ala Pro Gly Arg Arg Arg 279            288            297            306            315            324
CAG CAG GCC CGG AAC CGC TCC ACC CCG GCC CAG GAC GTG TCG CGG GCC TCC AGC
Gln Gln Ala Arg Asn Arg Ser Thr Pro Ala Gln Asp Val Ser Arg Ala Ser Ser 333            342            351            360            369            378
GCC TCA GAC TAC AAC AGC AGC GAG CTG AAG ACG GCC TGC CGG AAG CAT GAG CTC
Ala Ser Asp Tyr Asn Ser Ser Glu Leu Lys Thr Ala Cys Arg Lys His Glu Leu 387            396            405            414            423            432
TAC GTG AGC TTC CAG GAC CTG GGG TGG CAG GAC TGG ATC ATT GCC CCC AAG GGC
Tyr Val Ser Phe Gln Asp Leu Gly Trp Gln Asp Trp Ile Ile Ala Pro Lys Gly 441            450            459            468            477            486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495            504            513            522            531            540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu 549            558            567            576            585            594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603            612            621            630            639            648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val 657            666            676            686            696            706
CGA GCG TGT GGG TGC CAC TGACTCGGGG TGAGTGGCTG GGGACGCTGT GCACACACTG
Arg Ala Cys Gly Cys His
                   (222)

716            726            736            746            756            766
CCTGGACTCC TGGATCACGT CCGCCTTAAG CCCACAGAGG CCCCCGGGAC ACAGGAGGAG 776            786            796            806            816            826
ACCCCGAGGC CACCTTCGGC TGGCGTTGGC CTTTCCGCCC AACGCAGACC CGAAGGGACC 836            846            856            866            876            886
CTGTCCGCCC CTTGCTCACA CCGTGAGCGT TGTGAGTAGC CATCGGGCTC TAGGAAGCAG

CACTCGAG
```

EXAMPLE V

Human BMP-5 Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single stranded M13 $^{32}$P-labeled probe corresponding to the above mentioned BMP-5 EcoRI-Bg1II fragment containing nucleotides 1–465 of the sequence of Table I. A strongly hybridizing band is detected in the lane corresponding to the human osteosarcoma cell line U-2OS RNA. Another nitrocellulose replica is hybridized to a single stranded M13 $^{32}$P-labeled probe containing the PstI-SmaI fragment of bovine BMP-6 (corresponding to nucleotides 106–261 of Table II). It is found that several RNA species in the lane corresponding to U-2OS RNA hybridize to this probe.

A cDNA library is made in the vector lambda ZAP (Stratagene) from U-2OS poly(A)-containing RNA using established techniques (Toole et al.). 750,000 recombinants of this library are plated and duplicate nitrocellulose replicas made. The SmaI fragment of bovine BMP-6 corresponding to nucleotides 259–751 of Table II is labeled by nick-translation and hybridized to both sets of filters in SHB at 65#. One set of filters is washed under stringent conditions (0.2× SSC, 0.1% SDS at 65#), the other under reduced stringency conditions (1× SSC, 0.1% SDS at 65#). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of Table II), and the third to the nick-translated BMP-5 XbaI fragments (nucleotides 1–76 of Table I). Hybridization and washes are carried out under stringent conditions.

17 clones that hybridized to the third probe more strongly than to the second probe are plaque purified. DNA sequence analysis of one of these, U2-16, indicated that it encodes human BMP-5. U2-16 was deposited with the American Type Culture Collection (ATCC), Rockville, Md. on Jun. 22, 1989 under accession number ATCC 68109. U2-16 contains an insert of approximately 2.1 Kb. The DNA sequence and derived amino acid sequence of U2-16 is shown below in Table III. This clone is expected to contain all of the nucleotide sequence necessary to encode the BMP-5 proteins. The cDNA sequence of Table III contains an open reading frame of 1362 bp, encoding a protein of 454 amino acids, preceded by a 5' untranslated region of 700 bp with stop codons in all frames, and contains a 3' untranslated region of 90 bp following the in frame stop codon (TAA).

This protein of 454 amino acids has a molecular weight of approximately 52,000 kd as predicted by its amino acid sequence, and is contemplated to represent the primary translation product. Based on knowledge of other BMP proteins and other proteins within the TGF-b family, cleavage of the precursor polypeptide may occur after the tribasic peptide Lys Arg Lys yielding a 132 amino acid mature peptide beginning with amino acid # 323 "Asn". However, the presence of di- or tribasic amino acid sequence is not an absolute requirement for proteolytic processing, as a number of prohormones are known to be processed after single arginines which conform to a consensus cleavage sequence arginine-X-X-arginine. It is therefore contemplated that the precursor polypeptide is proteolytically processed after the Arg-Ser-Val-Arg sequence yielding a polypeptide comprising 138 amino acids from amino acid #317 (Ala) to #454 (His) as shown in Table III with a calculated molecular weight of 15.6 kD. The processing of BMP-5 into the mature form is expected to involve dimerization and removal of the N-terminal region in a manner analogous to the processing of the related protein TGF-b [L. E. Gentry, et al., *Molec. & Cell. Biol.* 8:4162 (1988); R. Dernyck, et al., *Nature* 316:701 (1985)].

It is contemplated therefore that the mature active species of BMP-5 comprises a homodimer of 2 polypeptide subunits each subunit comprising amino acid #323–#454 with a predicted molecular weight of approximately 15,000 daltons. Further active BMP-5 species are contemplated, for example, proprotein dimers or proprotein subunits linked to mature subunits. Additional active species may comprise amino acid #329–#454 such species including homologous the tryptic sequences found in the purified bovine material. Also contemplated are BMP-5 proteins comprising amino acids #353–#454 thereby including the first conserved cysteine residue The underlined sequence of Table III from amino acid #329 to #337 Ser-Ser-Ser-His-Gln-Asp-Ser-Ser-Arg shares homology with the bovine sequence of Table I from amino acid #15 to #23 as discussed above in Example IV. Each of these sequences shares homology with a tryptic fragment sequence Ser-Thr-Pro-Ala-Gln-Asp-Val-Ser-Arg found in the 28,000–30,000 dalton purified bone preparation (and its reduced form at approximately 18,000–20,000 daltons) as described in the "BMP" co-pending applications mentioned above.

The underlined sequence of Table III from amino acid #356 to #362 His-Glu-Leu-Tyr-Val-Ser-Phe corresponds to the tryptic fragment identified in the bovine bone preparation described above from which the oligonucleotide probes are designed.

TABLE III

Human

| 10 | 20 | 30 | 40 | 50 |
|---|---|---|---|---|
| CTGGTATATT | TGTGCCTGCT | GGAGGTGGAA | TTAACAGTAA | GAAGGAGAAA |

| 60 | 70 | 80 | 90 | 100 |
|---|---|---|---|---|
| GGGATTGAAT | GGACTTACAG | GAAGGATTTC | AAGTAAATTC | AGGGAAACAC |

| 110 | 120 | 130 | 140 | 150 |
|---|---|---|---|---|
| ATTTACTTGA | ATAGTACAAC | CTAGAGTATT | ATTTTACACT | AAGACGACAC |

| 160 | 170 | 180 | 190 | 200 |
|---|---|---|---|---|
| AAAAGATGTT | AAAGTTATCA | CCAAGCTGCC | GGACAGATAT | ATATTCCAAC |

TABLE III-continued

Human

```
         210        220        230        240        250
ACCAAGGTGC AGATCAGCAT AGATCTGTGA TTCAGAAATC AGGATTTGTT 260        270        280        290        300
TTGGAAAGAG CTCAAGGGTT GAGAAGAACT CAAAAGCAAG TGAAGATTAC 310        320        330        340        350
TTTGGGAACT ACAGTTTATC AGAAGATCAA CTTTTGCTAA TTCAAATACC 360        370        380        390        400
AAAGGCCTGA TTATCATAAA TTCATATAGG AATGCATAGG TCATCTGATC 410        420        430        440        450
AAATAATATT AGCCGTCTTC TGCTACATCA ATGCAGCAAA AACTCTTAAC 460        470        480        490        500
AACTGTGGAT AATTGGAAAT CTGAGTTTCA GCTTTCTTAG AAATAACTAC 510        520        530        540        550
TCTTGACATA TTCCAAAATA TTTAAAATAG GACAGGAAAA TCGGTGAGGA 560        570        580        590        600
TGTTGTGCTC AGAAATGTCA CTGTCATGAA AAATAGGTAA ATTTGTTTTT 610        620        630        640        650
TCAGCTACTG GGAAACTGTA CCTCCTAGAA CCTTAGGTTT TTTTTTTTTT 660        670        680        690        700
AAGAGGACAA GAAGGACTAA AAATATCAAC TTTTGCTTTT GGACAAAA
```

TABLE III(a)

```
701              710          719          728          737
ATG CAT CTG ACT GTA TTT TTA CTT AAG GGT ATT GTG GGT TTC CTC
MET His Leu Thr Val Phe Leu Leu Lys Gly Ile Val Gly Phe Leu
(1)

746              755          764          773          782
TGG AGC TGC TGG GTT CTA GTG GGT TAT GCA AAA GGA GGT TTG GGA
Trp Ser Cys Trp Val Leu Val Gly Tyr Ala Lys Gly Gly Leu Gly 791              800          809          818          827
GAC AAT CAT GTT CAC TCC AGT TTT ATT TAT AGA AGA CTA CGG AAC
Asp Asn His Val  His Ser Ser Phe Ile Tyr Arg Arg Leu Arg Asn 836              845          854          863          872
CAC GAA AGA CGG GAA ATA CAA AGG GAA ATT CTC TCT ATC TTG GGT
His Glu Arg Arg Glu Ile Gln Arg Glu Ile Leu Ser Ile Leu Gly 881              890          899          908          917
TTG CCT CAC AGA CCC AGA CCA TTT TCA CCT GGA AAA ATG ACC AAT
Leu Pro His Arg Pro Arg Pro Phe Ser Pro Gly Lys Gln Ala Ser 926              935          944          953          962
CAA GCG TCC TCT GCA CCT CTC TTT ATG CTG GAT CTC TAC AAT GCC
Ser Ala Pro Leu Phe MET Leu Asp Leu Tyr Asn Ala MET Thr Asn 971              980          989          998         1007
GAA GAA AAT CCT GAA GAG TCG GAG TAC TCA GTA AGG GCA TCC TTG
Glu Glu Asn Pro Glu Glu Ser Glu Tyr Ser Val Arg Ala Ser Leu 1016            1025         1034         1043         1052
GCA GAA GAG ACC AGA GGG GCA AGA AAG GGA TAC CCA GCC TCT CCC
Ala Glu Glu Thr Arg Gly Ala Arg Lys Gly Tyr Pro Ala Ser Pro 1061            1070         1079         1088         1097
AAT GGG TAT CCT CGT CGC ATA CAG TTA TCT CGG ACG ACT CCT CTG
Asn Gly Tyr Pro Arg Arg Ile Gln Leu Ser Arg Thr Thr Pro Leu 1106            1115         1124         1133         1142
ACC ACC CAG AGT CCT CCT CTA GCC AGC CTC CAT GAT ACC AAC TTT
```

TABLE III(a)-continued

Thr Thr Gln Ser Pro Pro Leu Ala Ser Leu His Asp Thr Asn Phe 1151        1160        1169        1178        1187
CTG AAT GAT GCT GAC ATG GTC ATG AGC TTT GTC AAC TTA GTT GAA
Leu Asn Asp Ala Asp MET Val MET Ser Phe Val Asn Leu Val Glu 1196        1205        1214        1223        1232
AGA GAC AAG GAT TTT TCT CAC CAG CGA AGG CAT TAC AAA GAA TTT
Arg Asp Lys Asp Phe Ser His Gln Arg Arg His Tyr Lys Glu Phe

TABLE III(b)

1241        1250        1259        1268        1277
CGA TTT GAT CTT ACC CAA ATT CCT CAT GGA GAG GCA GTG ACA GCA
Arg Phe Asp Leu Thr Gln Ile Pro His Gly Glu Ala Val Thr Ala 1286        1295        1304        1313        1322
GCT GAA TTC CGG ATA TAC AAG GAC CGG AGC AAC AAC CGA TTT GAA
Ala Glu Phe Arg Ile Tyr Lys Asp Arg Ser Asn Asn Arg Phe Glu 1331        1340        1349        1358        1367
AAT GAA ACA ATT AAG ATT AGC ATA TAT CAA ATC ATC AAG GAA TAC
Asn Glu Thr Ile Lys Ile Ser Ile Tyr Gln Ile Ile Lys Glu Tyr 1376        1385        1394        1403        1412
ACA AAT AGG GAT GCA GAT CTG TTC TTG TTA GAC ACA AGA AAG GCC
Thr Asn Arg Asp Ala Asp Leu Phe Leu Leu Asp Thr Arg Lys Ala 1421        1430        1439        1448        1457
CAA GCT TTA GAT GTG GGT TGG CTT GTC TTT GAT ATC ACT GTG ACC
Gln Ala Leu Asp Val Gly Trp Leu Val Phe Asp Ile Thr Val Thr 1466        1475        1484        1493        1502
AGC AAT CAT TGG GTG ATT AAT CCC CAG AAT AAT TTG GGC TTA CAG
Ser Asn His Trp Val Ile Asn Pro Gln Asn Asn Leu Gly Leu Gln 1511        1520        1529        1538        1547
CTC TGT GCA GAA ACA GGG GAT GGA CGC AGT ATC AAC GTA AAA TCT
Leu Cys Ala Glu Thr Gly Asp Gly Arg Ser Ile Asn Val Lys Ser 1556        1565        1574        1583        1592
GCT GGT CTT GTG GGA AGA CAG GGA CCT CAG TCA AAA CAA CCA TTC
Ala Gly Leu Val Gly Arg Gln Gly Pro Gln Ser Lys Gln Pro Phe 1601        1610        1619        1628        1637
ATG GTG GCC TTC TTC AAG GCG AGT GAG GTA CTT CTT CGA TCC GTG
MET Val Ala Phe Phe Lys Ala Ser Glu Val Leu Leu Arg Ser Val 1646        1655        1664        1673        1682
AGA GCA GCC AAC AAA CGA AAA AAT CAA AAC CGC AAT AAA TCC AGC
Arg Ala Ala Asn Lys Arg Lys Asn Gln Asn Arg Asn Lys <u>Ser Ser</u>
                                                    (329)

1691        1700        1709        1718        1727
TCT CAT CAG GAC TCC TCC AGA ATG TCC AGT GTT GGA GAT TAT AAC
<u>Ser His Gln Asp Ser Ser Arg</u> MET Ser Ser Val Gly Asp Tyr Asn
              (337)

TABLE III(c)

1736        1745        1754        1763        1772
ACA AGT GAG CAA AAA CAA GCC TGT AAG AAG CAC GAA CTC TAT GTG
Thr Ser Glu Gln Lys Gln Ala Cys Lys Lys <u>His Glu Leu Tyr Val</u>
                                          (356)

1781        1790        1799        1808        1817
AGC TTC CGG GAT CTG GGA TGG CAG GAC TGG ATT ATA GCA CCA GAA
<u>Ser Phe</u> Arg Asp Leu Gly Trp Gln Asp Trp Ile Ile Ala Pro Glu

TABLE III(c)-continued (362)

```
1826          1835          1844          1853          1862
GGA TAC GCT GCA TTT TAT TGT GAT GGA GAA TGT TCT TTT CCA CTT
Gly Tyr Ala Ala Phe Tyr Cys Asp Gly Glu Cys Ser Phe Pro Leu 1871          1880          1889          1898          1907
AAC GCC CAT ATG AAT GCC ACC AAC CAC GCT ATA GTT CAG ACT CTG
Asn Ala His MET Asn Ala Thr Asn His Ala Ile Val Gln Thr Leu 1916          1925          1934          1943          1952
GTT CAT CTG ATG TTT CCT GAC CAC GTA CCA AAG CCT TGT TGT GCT
Val His Leu MET Phe Pro Asp His Val Pro Lys Pro Cys Cys Ala 1961          1970          1979          1988          1997
CCA ACC AAA TTA AAT GCC ATC TCT GTT CTG TAC TTT GAT GAC AGC
Pro Thr Lys Leu Asn Ala Ile Ser Val Leu Tyr Phe Asp Asp Ser 2006          2015          2024          2033          2042
TCC AAT GTC ATT TTG AAA AAA TAT AGA AAT ATG GTA GTA CGC TCA
Ser Asn Val Ile Leu Lys Lys Tyr Arg Asn MET Val Val Arg Ser
                                            (450)

2051          2060          2070          2080          2090          2100
TGT GGC TGC CAC TAATATTAAA TAATATTGAT AATAACAAAA AGATCTGTAT
Cys Gly Cys His 2110          2120          2130          2140          2150
TAAGGTTTAT GGCTGCAATA AAAAGCATAC TTTCAGACAA ACAGAAAAAA AAA
```

The invention encompasses the corresponding bovine and human BMP-5 genomic sequences. These genes can be isolated using the cDNA sequences set forth in Table I and Table III as probes to screen genomic libraries using techniques known to those skilled in the art.

When the tryptic sequence His-Glu-Leu-Tyr-Val-Ser-Phe-(Ser) described above was identified, it was noted to be similar to the sequence His-Pro-Leu-Tyr-Val-Asp-Phe-Ser found in the bovine and human cartilage/bone protein BMP-2A sequence, as described in co-pending U.S. application Ser. No. 179,100. Human BMP-5 shares homology with other BMP molecules as well as other members of the TGF-b superfamily of molecules. The cysteine-rich carboxy-terminal 102 amino acids residues of human BMP-5 shares the following homologies with BMP proteins disclosed in copending applications described above: 61% identity with BMP-2; 43% identity with BMP-3, 59% identity with BMP-4; 91% identity with BMP-6; and 88% identity with BMP-7. Human BMP-5 further shares the following homologies: 38% identity with TGF-b3; 37% identity with TGF-b2; 36% identity with TGF-b1; 25% identity with Mullerian Inhibiting Substance (MIS), a testicular glycoprotein that causes regression of the Mullerian duct during development of the male embryo; 25% identity with inhibin a; 38% identity with inhibin $b_B$; 45% identity with inhibin $b_A$; 56% identity with Vg1, a Xenopus factor which may be involved in mesoderm induction in early embryogenesis (Lyons, et al., *PNAS USA* 86:4554–4558 (1989)]; and 57% identity with Dpp the product of the Drosophila decapentaplegic locus which is required for dorsal-ventral specification in early embryogenesis and is involved in various other developmental processes at later stages of development [Padgett, et al., *Nature* 325:81–84 (1987)].

The procedures described above and additional methods known to those skilled in the art may be employed to isolate other related proteins of interest by utilizing the bovine or human proteins as a probe source. Such other proteins may find similar utility in, inter alia, fracture repair, wound healing and tissue repair.

EXAMPLE VI

Expression of the BMP-5 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention may be stably transformed mammalian cells. For transient expression, the cell line of choice is SV40 transformed African green monkey kidney COS-1 or COS-7 which typically produce moderate amounts of the protein encoded within the plasmid for a period of 1–4 days. For stable high level expression, it is further contemplated that the preferred mammalian cells will be Chinese hamster ovary (CHO) cells.

The transformed host cells are cultured and the BMP-5 protein expressed thereby is recovered, isolated and purified. Characterization of expressed proteins is carried out using standard techiques. For example, characterization may include pulse labeling with [$^{35}$S] methionine or cysteine and analysis by polyacrylamide electrphoresis. The recombinantly expressed BMP-5 proteins are free of proteinaceous materials with which they are co-produced and with which they ordinarily are associated in nature, as well as from other contaminants, such as materials found in the culture media.

In order to express biologically active human BMP-5 a selected host cell is transformed, using techniques known to those skilled in the art of genetic engineering, with a DNA sequence encoding human BMP-5 protein. The DNA comprises the nucleotide sequence from nucleotide #1665 to #2060 set forth in Table III encoding amino acid #323 to #454. The DNA may comprise the DNA sequence from nucleotide # 699 to # 2060 set forth in Table III. The transformed host cells are cultured and the BMP-5 protein comprising the amino acid sequence from amino acid # 323 to amino acid # 454 set forth in Table III is expressed. The expressed protein is recovered, isolated and purified from the culture and culture medium. The purified protein is substantially free from other proteinaceous materials with which it is co-produced, and from other contaminants.

A. Vector Construction

As described above, numerous expression vectors known in the art may be utilized in the expression of BMP proteins of the invention. The vector utilized in the following examples are pMT21, a derivitive of pMT$_2$, and pEMC2b1 derived from pMT21 though other vectors may be suitable in practice of the invention.

pMT$_2$ is derived from pMT2-VWF, which has been deposited with the American Type Culture Collection (ATCC), Rockville, Md. (U.S.A.) under accession number ATCC 67122 under the provisions of the Budapest Treaty. EcoRI digestion excises the cDNA insert present in pMT-VWF, yielding pMT2 in linear form which can be ligated and used to transform *E. coli* HB 101 or DH-5 to ampicillin resistance. Plasmid pMT2 DNA can be prepared by conventional methods.

pMT21 is then constructed using loopout/in mutagenesis [Morinaga, et al., *Biotechnology* 84:636 (1984)]. This removes bases 1075 to 1170 (inclusive). In addition it inserts the following sequence: 5' TCGA 3'. This sequence completes a new restriction site, XhoI. This plasmid now contains 3 unique cloning sites PstI, EcoRI, and XhoI.

In addition, pMT21 is digested with EcoRV and XhoI, treating the digested DNA with Klenow fragment of DNA polymerase I and ligating ClaI linkers (NEBio Labs, CATCGATG). This removes bases 2171 to 2420 starting from the HindIII site near the SV40 origin of replication and enhancer sequences of pMT2 and introduces a unique Cla I site, but leaves the adenovirus VAI gene intact.

pEMC2b1 is derived from pMT21. pMT21 is cut with EcoRI and XhoI which cleaves the plasmid two adjacent cloning sites situated after the IgG intron. An EMCV fragment of 508 base pairs is cut from pMT$_2$ECAT$_1$ [S. K. Jong, et al., *J. Virol.* 63:1651–1660 (1989)] with the restriction enzymes EcoRI and TaqaI. A pair of oligonucleotides 68 nucleotides cga ggttaaaaaa cgtctaggcc ccccgaacca cggg-gacgtg gttttccttt gaaaaacacg attgc in length are synthesized to duplicate the EMCV sequence up to the ATG. The ATG is changed to an ATT, and a C is added, creating a XhoI site at the 3' end. A tagαI site is situated at the 5' end. Ligation of the MT21 EcoRI to XhoI fragment to the EMCV EcoRI to TaqαI fragment and to the TagαI/XhoI oligonucleotides produces the vector EMC@B1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the dadenovirus VAI gene, DHFR and B-lactamase markers and an EMC sequence, in appropriate relationships to direct the high level expression of the desired cDNA in mammalian cells.

B. BMP-5 Vector Construction

A derivative of the BMP-5 cDNA sequence set forth in Table III comprising the the nucleotide sequence from nucleotide #699 to #2070 is specifically amplified. The oligonucleotides CGACCTGCAGCCACCATGCATCT-GACTGTA and TGCCTGCAGTTTAATATTAGTG-GCAGC are utilized as primers to allow the amplification of nucleotide sequence #699 to #2070 of Table III from the insert of clone U2-16 described above in Example V. This procedure introduces the nucleotide sequence CGACCTG-CAGCCACC immediately preceeding nucleotide #699 and the nucleotide sequence CTGCAGGCA immediately following nucleotide #2070. The addition of these sequences results in the creation of PstI restriction endonuclease recognition sites at both ends of the amplified DNA fragment. The resulting amplified DNA product of this procedure is digested with the restriction endonuclease PstI and subcloned into the PstI site of the pMT2 derivative pMT21 described above. The resulting clone is designated H5/5/pMT.

The insert of H5/5/pMT is excised by PstI digestion and subcloned into the plasmid vector pSP65 at. the PstI site resulting in BMP5/SP6. BMP5/SP6 and U2-16 are digested with the restriction endonucleases NsiI and NdeI to excise the portion of their inserts corresponding to nucleotides #704 to #1876 of Table III. The resulting 1173 nucleotide NsiI-Ndei fragment of clone U2-16 is ligated into the NsiI-NdeI site of BMP5/SP6 from which the corresponding 1173 nucleotide NsiI-NdeI fragment had been removed. The resulting clone is designated BMP5mix/SP64.

Direct DNA sequence analysis of BMP5mix/SP64 is performed to confirm identity of the nucleotide sequences produced by the amplification to those set forth in Table III. The clone BMP5mix/SP64 is digested with the restriction endonuclease PstI resulting in the excision of an insert comprising the nucleotides #699 to #2070 of Table III and the additional sequences containing the PstI recognition sites as described above. The resulting 1382 nucleotide PstI fragment is subcloned into the PstI site of the pMT2 derivative pMT21 and pEMC2b1. These clones are designated BMP5mix/pMT21#2 and BMp5mix/EMC#11.

EXAMPLE VII

Transient COS Cell Expression

To obtain transient expression of BMP-5 proteins a vector containing the cDNA for BMP-5, BMP5mix/pMT21#2, is transfected into COS-1 cells using the electroporation method. Other suitable transfection methods include DEAE-dextran, and lipofection. Approximately 48 hours later, cells are analysed for expression of both intracellular and secreted BMP-5 protein by metabolic labelling with [$^{35}$S] methionine and polyacrylamide gel electrophoresis. Intracellular BMP is analyzed in cells which are treated with tunicamycin, an inhibitor of N-linked glycosylation. In tunicamycin-treated cells, the nonglycosylated primary translation product migrates as a homogeneous band of predictable size and is often easier to discern in polyacrylamide gels than the glycosylated form of the protein. In each case, intracelluar protein in tunicamycin-treated cells is compared to a duplicate plate of transfected, but untreated COS-1 cells.

The results demonstrate that intracellular forms of BMP-5 of approximately 52 Kd and 57 Kd are made by COS cells. The 52 Kd protein is the size predicted by the primary sequence of the the BMP-5 cDNA clone. Following treatment of the cells with tunicamycin, only the 52 Kd form of BMP-5 is made, suggesting that the 57 Kd protein is a glycosylated derivative of the 52 Kd primary translation product. The 57 Kd protein is secreted into the conditioned medium and is apparently not efficiently processed by COS-1 cells into the pro and mature peptides.

EXAMPLE VIII

CHO Cell Expression

DHFR deficient CHO cells (DUKX B11) are transfected by electroporation with BMP-5 expression vectors described above, and selected for expression of DHFR by growth in nucleoside-free media. Other methods of transfection, including but not limited to $CaPO_4$ precipitation, protoplast fusion, microinjection, and lipofection, may also be employed. In order to obtain higher levels of expression more expediently, cells may be selected in nucleoside-free media supplemented with 5 nM, 20 nM or 100 nM MTX. Since the DHFR selectable marker is physically linked to the BMP-5 cDNA as the second gene of a bicistronic coding region, cells which express DHFR should also express the BMP-5 encoded within the upstream cistron. Either single clones, or pools of combined clones, are expanded and analyzed for expression of BMP protein. Cells are selected in stepwise increasing concentrations of MTX (5 nM, 20 nM, 100 nM, 500 nM, 2 uM, 10 uM, and 100 uM) in order to obtain cell lines which contain multiple copies of the expression vector DNA by virtue of gene amplification, and hence secrete large amounts of BMP-5 protein.

Using standard techniques cell lines are screened for expression of BMP-5 RNA, protein or activity, and high expressing cell lines are cloned or recloned at the appropriate level of selection to obtain a more homogeneous population of cells. The resultant cell line is then further characterized for BMP-5 DNA sequences, and expression of BMP-5 RNA and protein. Suitable cell lines can then be used for producing recombinant BMP protein.

The BMP-5 vector BMP5mix/pMT21#2 and BMP5mix/EMC#11 described above are transfected into CHO cells by electroporation, and cells are selected for expression of DHFR in nucleoside free medium. Clonal cell lines are obtained from individual colonies and are subsequently selected stepwise for resistance to MTX, and are analyzed for secretion of BMP-5 proteins. In some cases cell lines may be maintained as pools and cloned at later stages of MTX selection. One particular cell line further described, is designated 5E10 is sequentially selected for resistence to 0.02 uM, 0.1 mM, 0.5 uM and 2.0 uM MTX to obtain amplified expression of BMP-5.

The amount of BMP-5 recovered in conditioned medium from 5E10 and other cell lines that express BMP-5 can be increased by including heparin, suramin, dextran sulfate, pectic acid, sodium sulfate, or related compounds in the growth medium.

As described in Example V. the cDNA for BMP-5 encodes a protein of approximately 52 kD. Following processing within the cell that includes, but may not be limited to, propeptide cleavage, glycosylation, and dimer or multimer formation, multiple BMP-5 peptides are produced. There are at least 4 candidate peptides for processed forms of the BMP-5 protein discernable following SDS PAGE under reducing conditions; a peptide of approximately 65 kD, a peptide of approximately 35 kD, and a doublet of approximately 22 kD molecular weight. Other less abundant BMP-5 peptides may also be present. By comparison to the processing of other related BMP molecules and the related protein TGF-beta, the 65 Kd protein likely represents unprocessed BMP-5, the 35 Kd species represents the propeptide, and the 22 Kd doublet represents the mature peptide.

Material from a BMP-5 cell line is analyzed in a 2-dimensional gel system. In the first dimension, proteins are electrophoresed under nonreducing conditions. The material is then reduced, and electrophoresed in a second polyacrylamide gel. Proteins that form disulfide-bonded dimers or multimers will run below a diagonal across the second reduced gel. Results from analysis of BMP-5 protein indicates that a significant amount of the mature BMP-5 peptides can form homodimers of approximately 30–35 kD that reduce to the 22 kD doublet observed in one dimensional reduced crels. A fraction of the mature peptides are apparently in a disulfide-bonded complex with the pro peptide. The amount of this complex is minor relative to the mature homodimer. In addition, some of the unprocessed protein can apparently form homodimers or homomultimers.

EXAMPLE IX

Purification and Biological Activity of Expressed BMP-5 Proteins

To measure the biological activity of the expressed BMP-5 proteins obtained in Example VIII above, the BMP-5 proteins are recovered from the culture media and purified by isolating them from other proteinaceous materials with which they are co-produced, as well as from other contaminants. BMP-5 proteins may be partially purified on a Heparin Sepharose column and further purified using standard purification techniques known to those skilled in the art. The BMP-5 protein is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-5 proteins of the invention have been added are removed from rats after approximately seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

A. Purification of BMP-5 Proteins (1) As one example of BMP-5 purification 4 ml of the collected post transfection conditioned medium supernatant from one 100 mm culture dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3–4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid.

Further purification may be achieved by preparative $NaDodSO_4$/PAGE [Laemmli, *Nature* 227:680–685 (1970)]. For instance, approximately 300 lg of protein is applied to a 1.5 -mm-thick 12.5% gel: recovery is estimated by adding L-[$^{35}$S]methionine-labeled BMP protein purified over heparin-Sepharose as described above. Protein may be visualized by copper staining of an adjacent lane [Lee, et al., *Anal. Biochem.* 166:308–312 (1987)]. Appropriate bands are excised and extracted in 0.1% $NaDodSO_4$/20 mM Tris, pH 8.0. The supernatant may be acidified with 10% $CF_3COOH$ to pH 3 and the proteins are desalted on 5.0×0.46 cm Vydac $C_4$ column (The Separations Group, Hesperia, Calif.) developed with a gradient of 0.1% $CF_3COOH$ to 90% acetonitrile/ 0.1% $CFF_3COOH$.

(2) In another example, soluble heparin (100 ug/ml) is removed from of BMP-5 protein in conditioned media from 5E10(2) 2.0MTX (described above) using butyl TSK hydrophobic interactive chrmatography (HIC). The conditioned media is brought to 2M NaCl by addition of solid NaCl. The conditioned media is then loaded on butyl TSK equilabrated in 2M NaCl, 50 mM Tris, pH 7.4 washed with 0 M NaCl, 50 mM Tris, Ph 7.4, followed by elution with 1% Np-40, 6M urea, 50 mM Tris, pH 7.4 resulting in approximately 98% removal of soluble heparin.

The resulting material is then subjected to heparin sepharose chromatography. The material is directly loaded onto a heparin column equilabrated in 50 mM Tris, 6M urea, 0M NaCl, washed and eluted with a gradient of 0–2M NaCl. This material is analyzed by western blot and the BMP-5 containing fractions (0.3–0.8 M NaCl) are pooled. The antibody is directed against the C-terminal presumed mature portion. Proteins of 35–40 kD non-reduced, 20–22 kD reduced, and higher molecular weight dimers are observed.

The BMP-5 containing fractions are concentrated and diafiltered to bring the sample to 0.1% TFA loaded onto a reverse phase column and eluted with a gradient from 30% to 60% B (A=0.1% TFA; B=0.1% TFA in 90% acetonitrile) in 75 min at 1 ml/min. SDS-PAGE analysis reveals several molecular weight species of BMP-5 proteins which are further described below. The mature species which is contemplated to comprise a homodimer of amino acids #317–#454 as shown in Table III comprises approximately 46–49% of the resulting molecular weight species.

B. Characterization of BMP-5 Proteins

One dimensional Western blot analysis reveals several molecular weight species including 98 kDa, 72 kDa 50 kDa and 35–40 kDa. Upon reduction the following species are seen 68 kDA, 43 kDa and 20–22 kDA. The non-reduced 98 kDa species is comtemplated to comprise a homodimer of two 50 kDa subunits each comprising amino acids #28 # 54 as shown in Table III. The 72 kDa species is contemplated to comprise a heterodimer of a 50 kDa subunit (comprising amino acids #28–#454 of Table III as described above) and a 20 kDa subunit comprising amino acids #317–#454 as shown in Table III. The 35–40 kDa species is contemplated to represent the mature species comprising a homodimer of two 20 kDa subunits each comprising amino acids #317–#454 as shown in Table III.

C. BMP-5 Activity

BMP-5 (containing 100 ug/ml soluble heparin) purified in a preliminary experiment over octyl-sepharose (HIC) [see description below] then over heparin sepharose in a manner similar to the butyl then heparin steps described above is mixed with 20 mg rat matrix and implanted for 10 days according to the rat ectopic assay described above in Example III. Approximately 1–3 ug BMP-5 protein from the heparin sepharose step results in the formation of cartilage and bone. The octyl-sepharose purification step is carried out by adding solid $(NH_4)_2SO_4$ to BMP-5 conditioned media containing 100 ug/ml soluble heparin to a final concentration of 1M. This is loaded onto a column of octly-sepharose equilabrated in 1M $(NH_4)_2SO_4$, 50 mM Tris pH 7.4. The column is washed with starting buffer then with 50 mM Tris pH 7.4 and eluted with 50 mM Tris, 6M urea, 0.2% octly glucoside pH 7.4. Purification over heparin sepharose is by step gradient, washed with 50 mM Tris, 0.15M NaCl, 6M urea pH 7.4, eluted with 50 mM Tris, 2M NaCl, 6M urea pH 7.4. The material implanted is 2M NaCl.

EXAMPLE X

W-20 Bioassays

A. Description of W-20 cells

Use of the W-20 bone marrow stromal cells as an indicator cell line is based upon the conversion of these cells to osteoblast-like cells after treatment with a BMP protein [Thies et al, *Journal of Bone and Mineral Research,* 5:305 (1990); and Thies et al, *Endocrinology,* 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 $\mu$l of media (DME with 10% heat inactivated fetal calf serum, 2 mM glutamine and 100 Units/ml penicillin+100 $\mu$g/ml streptomycin. The cells are allowed to attach overnight in a 95% air, 5% $CO_2$ incubator at 37° C. The 200 $\mu$l of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 $\mu$l per well of calcium/magnesium free phosphate buffered saline and these washes are discarded. 50 $\mu$l of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 $\mu$l of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 $\mu$l of 0.2N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

| Absorbance Values for Known Standards of P-Nitrophenol Phosphate | |
|---|---|
| P-nitrophenol phosphate umoles | Mean absorbance (405 nm) |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to $\mu$moles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-5 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE XI

Using Northern analysis, BMP-5 and BMP-5-related proteins can be tested for their effects on various cell lines. Suitable cell lines include cell lines derived from E13 mouse limb buds. After 10 days of treatment with BMP-5 or BMP-5-related protein, the cell phenotype is examined histologically for indications of tissue differentiation. In addition, Northern analysis of mRNA from BMP-5 or BMP-5-related protein treated cells can be performed for various markers including one or more of the following markers for bone, cartilage and/or tendon/ligament, as described in Table IV:

TABLE IV

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels

EXAMPLE XII

Embryonic Stem Cell Assay

In order to assay the effects of the BMP-5 proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for inducing bone and/or cartilage formation in a patient in need thereof comprising administering to said patient an effective amount of a composition comprising a matrix, a pharmaceutically acceptable vehicle, and a protein selected from the group consisting of:
  (a) a purified dimeric BMP-5 protein comprising the amino acid sequence from amino acid #1 or 28 or 317 (Ala) or 328 to amino acid #454 (His) as shown in Table III; and
  (b) naturally occurring allelic sequences thereof.

2. The method of claim 1 wherein the protein is encoded by the BMP-5 DNA sequence of ATCC 68019.

* * * * *